United States Patent
Simoulidis et al.

(10) Patent No.: US 7,678,382 B2
(45) Date of Patent: Mar. 16, 2010

(54) SINGLE-CRYSTAL PLATY BARIUM SULFATE IN COSMETIC COMPOSITIONS

(75) Inventors: Sofia Simoulidis, Norwalk, CT (US); Marcina Siciliano, New Haven, CT (US); Jack Polonka, Peekskill, NY (US)

(73) Assignee: Conopco, Inc., Englewood Cliffs, NJ (US)

( * ) Notice: Subject to any disclaimer, the term of this patent is extended or adjusted under 35 U.S.C. 154(b) by 357 days.

(21) Appl. No.: 11/682,893

(22) Filed: Mar. 7, 2007

(65) Prior Publication Data

US 2008/0152682 A1 Jun. 26, 2008

Related U.S. Application Data

(60) Provisional application No. 60/871,485, filed on Dec. 22, 2006.

(51) Int. Cl.
*A61K 8/02* (2006.01)
(52) U.S. Cl. ...................................... 424/401
(58) Field of Classification Search .................. 424/401
See application file for complete search history.

(56) References Cited

U.S. PATENT DOCUMENTS

| | | | |
|---|---|---|---|
| 5,171,572 | A | 12/1992 | Suganuma et al. |
| 5,262,148 | A | 11/1993 | Sugasawa et al. |
| 5,972,359 | A | 10/1999 | Sine et al. |
| 5,997,890 | A | 12/1999 | Sine et al. |
| 6,174,533 | B1 | 1/2001 | SaNogueira, Jr. et al. |
| 6,432,389 | B1 | 8/2002 | Hansenne et al. |
| 6,495,123 | B1 * | 12/2002 | Faryniarz et al. ............ 424/59 |
| 7,033,614 | B2 | 4/2006 | Linz et al. |
| 7,182,949 | B2 * | 2/2007 | Dalko et al. ................ 424/400 |
| 2001/0007677 | A1 * | 7/2001 | Nagatani et al. ............ 424/401 |
| 2003/0003065 | A1 * | 1/2003 | Kalla et al. .................. 424/63 |
| 2003/0180535 | A1 * | 9/2003 | Horino et al. ............... 428/384 |
| 2005/0079190 | A1 * | 4/2005 | Polonka ..................... 424/401 |
| 2005/0287092 | A1 * | 12/2005 | Liechty et al. ................ 424/63 |

FOREIGN PATENT DOCUMENTS

| | | | |
|---|---|---|---|
| JP | 2004-107221 | | 4/2004 |
| JP | 2004107221 | * | 4/2004 |
| JP | 2006-291156 | | 10/2006 |
| WO | 2007/141916 A1 | | 12/2007 |

OTHER PUBLICATIONS

Robert A. Charvat. Coloring of Plastics: Fundamentals. 2nd Edition. p. 343, Table 23.1. (2004).*
Sakiguchi et al., JP 2004107221. Machine translation.*
International Search Report.

* cited by examiner

*Primary Examiner*—David J Blanchard
*Assistant Examiner*—Nicoletta Kennedy
(74) *Attorney, Agent, or Firm*—Milton L. Honig

(57) ABSTRACT

A cosmetic composition is provided which includes from 0.01 to 10% of single-crystal platy barium sulfate, from 0.5 to 10% of a water insoluble powdered acrylic polymer in porous particle form and a carrier. The compositions have soft focus optics imparting radiance to the applied skin area without excessive shininess or opacity and have excellent skinfeel properties.

7 Claims, No Drawings

SINGLE-CRYSTAL PLATY BARIUM SULFATE IN COSMETIC COMPOSITIONS

BACKGROUND OF THE INVENTION

1. Field of the Invention

The invention relates to compositions for improving the appearance of skin, particularly to provide good coverage over imperfections such as pores and uneven skin tone, while retaining a natural skin appearance.

2. The Related Art

A matte effect is often sought from facially applied cosmetics. The matte finish overcomes the shiny effect engendered by greasy skin, particularly under hot and humid conditions. Absorbent fillers such as talc, silica, kaolin and other inorganic particulates have been used to achieve the effect by their optical properties.

Imperfect skin can be hidden in two ways through manipulation of light transmission. In the first, components of the cosmetic may simply reflect light back toward the source. An alternative approach is referred to as achieving a soft focus effect. Here the incoming light is distorted by scattering (lensing). Components of the color cosmetic in this mechanism operate as lenses to bend and twist light into a variety of directions.

While it is desirable to hide imperfect skin through a matte effect, there is also a desire to achieve a healthy skin radiance. A cosmetic covering that is too opaque hides the skin under a paint-like coating. Imperfections are hidden but there is no radiance. Some refer to this as whitening. Where light transmission is insufficiently hindered, the opposite occurs. Here the glow may be healthy but aesthetically displeasing skin topography and color may now be apparent.

U.S. Pat. No. 5,997,890 (Sine et al.), U.S. Pat. No. 5,972,359 (Sine et al.), and U.S. Pat. No. 6,174,533 B1 (SaNogueira, Jr.) are all directed to topical compositions to provide good coverage of skin imperfections. The solution proposed by these documents is the use of a metal oxide with a refractive index of at least about 2 and a neat primary particle size of from about 100 to about 300 nm. Preferred particulates are titanium dioxide, zirconium oxide and zinc oxide.

A significant disadvantage of titanium dioxide and zinc oxide is the whitening effect upon the skin. An undesirable ashen appearance is unfortunately created.

U.S. Patent Application 2005/0287092 A1 (Liechty et al.) reports make-up and skincare compositions in powder form which allow the natural grain of the skin to show through. These powders are based upon barium sulfate particles coated with an N-acylamino acid such as lauroyllysine. Also present is at least one elastomeric organopolysiloxane powder or a polymethylmethacrylate powder.

U.S. Patent Application 2005/0079190 A1 (Polonka) discloses the use of solid single-crystal flat platy particles which in cosmetic skin care compositions provide consumer-desired properties of the appearance of natural skin radiance. Suitable platy particles include bismuth oxychloride, aluminum oxide, zirconium oxide and boron nitride.

U.S. Pat. No. 6,495,123 (Faryniarz et al.) and U.S. Pat. No. 6,432,389 B1 (Hansenne et al.) describe cosmetic compositions with improved skinfeel properties delivered through polymeric porous particles such as methyl methacrylate crosspolymers.

A challenge which has not been fully met by the known art is delivery of a composition with appropriate optics to achieve both soft focus and radiance properties in a system that still provides excellent skinfeel. Still further there is a need which has not previously been fully met for a soft focus system that reduces "red wavelength" to hide fine lines and wrinkles.

SUMMARY OF THE INVENTION

A cosmetic composition is provided which includes:
(i) from about 0.01 to about 10% of single-crystal platy barium sulfate by weight of the composition;
(ii) from about 0.1 to about 10% of a water-insoluble powdered acrylic polymer in porous particle form, and
(iii) a cosmetically acceptable carrier

DETAILED DESCRIPTION OF THE INVENTION

Now it has been found that a combination of single-crystal platy barium sulfate and a water-insoluble powdered acrylic polymer in porous particle form provide a cosmetic composition which applied to the face achieves soft focus with radiance effect. The treated facial area achieves a natural end-finish. Skinfeel is excellent without drawbacks associated with inorganic particulate formulated cosmetics.

The inventive compositions employ solid particles that are single-crystal, flat and platy, to impart a radiant appearance to the skin upon application. By virtue of being flat single crystals, the particles deliver high reflectance. Flat platy crystals can generate this natural radiant appearance via optical reflectance. The number average (diameter) particle size may range from about 0.1 to about 30 micron, but preferably from 6 to 18 micron, and optimally from 8 to 15 micron.

Size of the platy particles is important because smaller particles reflect too little light to be readily apparent, while larger particles would be visible as discrete objects and thereby provide too much glitter or reflectance. The reflectance (index of refraction) of the platy crystal cannot be too high. Too high of an index of refraction will inhibit the transmission of natural skin color and create a cosmetic sheen. With too low an index of refraction, the particles will have approximately the same index of refraction as the skin or the product film, resulting in a weak reflectance, thereby diminishing the appearance of radiance.

Single-crystal structure is also key because the smoothness of the crystal surface minimizes opacity or diffuse scattering effects, which would lead to an artificial cosmetic effect. Single-crystal structure maximizes the smooth crystalline surface area. As the facet of a crystal is the smoothest surface possible, it maximizes the degree of reflectance while minimizing the opacity. The product is designed to impart radiance while maintaining natural skin tone, which is achieved by controlling the Opacity of the composition.

The single-crystal, flat platy particles of this invention are barium sulfate. These particles preferably are not coated, especially not coated with organic coatings such as N-acyl amino acids (e.g. lauroyllysine). Amounts of the barium sulfate may range from about 0.01 to about 10%, preferably from about 0.1 to about 5%, more preferably from about 0.1 to about 1%, optimally from about 0.2 to about 0.5% by weight of the composition.

A second element of compositions according to the present invention is that of a water-insoluble powdered acrylic polymer in porous particle form. By the term "porous" is meant an open or closed cell structure. Preferably the particles are spherical but not hollow beads. Average particle size may range from about 0.1 to about 100, preferably from about 1 to about 50, more preferably greater than 5 and especially from 5 to about 16, optimally from about 6 to about 10 micron. Acrylic polymers of this invention can be formed from acrylic monomers including acrylic acid, methacrylic acid, methylacrylate, ethylacrylate, acrylamide and mixtures thereof. Additionally the acrylic polymers may be copolymers formed from copolymerization of acrylic monomers with non-acrylic monomers selected from ethylene, propylene, maleic acid, acrylonitrile, vinyl pyrrolidone, butadiene, styrene, octene, vinyl chloride, vinylidene chloride and mixtures thereof. The polymers are especially useful in cross-linked form. Cells of the porous polymer may be filled by a gas which can be air, nitrogen or a hydrocarbon. Oil Absorbance (castor oil) is a measure of porosity and may range from about 90 to about 500, preferably from about 100 to about 200, optimally from about 120 to about 180 ml/100 grams. Density of the particles may range from about 0.08 to 0.55, preferably from about 0.15 to 0.48 g/cm$^3$.

Particularly preferred for this invention is a synthetic copolymer of methyl methacrylate crosslinked with glycol dimethacrylate. It has the empirical formula:

$$(C_{10}H_{14}O_4\text{-}C_5H_8O_2)_x$$

and has been assigned Chemical Abstracts Service (CAS) No. 25777-71-3. It is also described at page 808, volume 1, *International Cosmetic Ingredient Dictionary and Handbook* (Seventh Edition, 1997), published by The Cosmetic, Toiletry, and Fragrance Association (Washington, D.C.). It is known by its INCI name of Methyl Methacrylate Crosspolymer.

Methyl Methacrylate Crosspolymer is commercially available from Presperse Incorporated, Piscataway, N.J., under the trademark Ganzpearl® GMP-0820. The product specifications of Ganzpearl® GMP-0820 include: spherical, white fine powder having a particle size of 4-10.5 µm, preferably 4-8 µm, high oil absorption, creamy feel, good slip, specific gravity of 1.10 to 1.25, film-forming, viscosity increasing. Its loss on ignition (400° C.) is less than 0.1%, and on drying (105° C./2 hours) is less than 2.0%. The surface residual monomer content of Ganzpearl® GMP-0820 is less than 20 ppm, with total residual monomer content being less than 100 ppm. The crosslinking density of this very high molecular weight polymer is circa 43 wt % [crosslinking monomer/(crosslinking monomer+base monomer)].

Methyl methacrylate crosspolymers are also commercially available from Nihon Junyaku under the trademark Jurymer MP-1P and from Tomer under the trademark Microsphere M-305.

Characteristically, the particulates of methyl methacrylate crosspolymers according to this invention have a particle size of less than 20 µm, preferably less than 10 µm.

Amounts of the water-insoluble acrylic polymer in porous particle form may range from about 0.01 to about 10%, preferably from about 0.1 to about 5%, optimally from about 0.3 to about 2% by weight of the composition.

Optionally other pigments may be useful in formulas of the present invention. Of special note are titanium dioxide, zinc oxide or zirconium oxide. Titanium dioxides may range in number average particle size from about 100 to about 800 nm, preferably from 400 to 500 nm. Zinc and zirconium oxides should be micronized having number average particle size less than 300 nm, preferably less than 200 nm, more preferably less than 100 nm and optimally less than 85 nm. Generally the particle sizes can range from about 0.01 to about 280 nm, more preferably from about 1 to about 200 nm, even more preferably from 10 to 95 nm, and optimally from 25 to 75 nm.

The amount of titanium oxide, zinc oxide or zirconium oxide may range from about 0.1 to about 20%, preferably from about 0.5 to about 10%, optimally from about 1 to about 5% by weight of the cosmetic composition.

A still further pigment type for purposes of this invention are the titanium dioxide coated micas. These include Timiron® MP-10 (particle size range 10,000-30,000 nm), Timiron® MP-14 (particle size range 5,000-30,000 nm), Timiron® MP-30 (particle size range 2,000-20,000 nm), Timiron® MP-101 (particle size range 5,000-45,000 nm), Timiron® MVP-111 (particle size range 5,000-40,000 nm), Timiron® MP-1001 (particle size range 5,000-20,000 nm), Timiron® MP-155 (particle size range 10,000-40,000 nm), Timiron® MP-175 (particle size range 10,000-40,000), Timiron® MP-115 (particle size range 10,000-40,000 nm), and Timiron® MP-127 (particle size range 10,000-40,000 nm). Most preferred is Timiron® MP-111 and the irredescent blue type known as Timiron® Silk Blue, both available from Rona/EM Industries, Inc., and mixtures thereof. The weight ratio of titanium dioxide coating to the mica platelet may range from about 1:10 to about 5:1, preferably from about 1:1 to about 1:6, more preferably from about 1:3 to about 1:4 by weight. The mica platelets may range from about 0.1 to about 5%, preferably from about 0.5 to about 3%, more preferably from about 0.8 to about 2%, optimally from about 1 to about 1.5% by weight of the composition.

A variety of materials may be present in the compositions to serve as cosmetically acceptable carriers. Foremost is water as a carrier. Amounts of water may range from about 1 to about 90%, preferably from about 30 to about 80%, optimally from about 50 to about 70% by weight of the composition.

Emollient materials may be included as carriers in compositions of this invention. These may be in the form of silicone oils, synthetic esters and hydrocarbons. Amounts of the emollients may range anywhere from about 0.1 to about 95%, preferably between about 1 and about 50% by weight of the composition.

Silicone oils may be divided into the volatile and nonvolatile variety. The term "volatile" as used herein refers to those materials which have a measurable vapor pressure at ambient temperature (20-25° C.). Volatile silicone oils are preferably chosen from cyclic (cyclomethicone) or linear polydimethylsiloxanes containing from 3 to 9, preferably from 4 to 5, silicon atoms. In many liquid versions of compositions according to the present invention, the volatile silicone oils may form a relatively large component of the compositions as carriers. Amounts may range from about 5% to about 80%, preferably from about 20% to about 70% by weight of the composition.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about 5×10$^{-6}$ to 0.1 m$^2$/s at 25° C. Among the preferred nonvolatile emollients useful in the present compositions are the polydimethyl siloxanes having viscosities from about 1×10$^{-5}$ to about 4×10$^{-4}$ m$^2$/s at 25° C.

Organopolysiloxane crosspolymers can be usefully employed. Representative of these materials are dimethicone/vinyl dimethicone crosspolymers and dimethicone crosspolymers available from a variety of suppliers including Dow Corning (9040, 9041, 9045, 9506 and 9509), General Electric (SFE 839), Shin Etsu (KSG-15, 16 and 18 [dimethiconelphenyl vinyl dimethicone crosspolymer]), and Grant Industries (Gransil brand of materials), and lauryl dimethicone/vinyl dimethicone crosspolymers supplied by Shin Etsu (e.g. KSG-31, KSG-32, KSG-41, KSG-42, KSG-43 and KSG-44). Amounts of the aforementioned silicone elastomers will usually be present from 0.1 to 20% by weight dissolved usually in a volatile silicone oil such as cyclomethicone.

When silicones are present in large amounts as carrier and water is also present, the systems may be oil continuous. These normally will require emulsification with a water-in-oil emulsifier such as a dimethicone copolyol (e.g. Abil EM-90 which is cetyl dimethicone copolyol).

Among the ester emollients are:

a) Alkenyl or alkyl esters of fatty acids having 10 to 20 carbon atoms. Examples thereof include isoarachidyl neopentanoate, isodecyl neopentanoate, isononyl isonanoate, cetyl ricinoleate, oleyl myristate, oleyl stearate, and oleyl oleate.

b) Ether-esters such as fatty acid esters of ethoxylated fatty alcohols.

c) Polyhydric alcohol esters. Ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols. Exemplative is pentaerythrityl tetraethylhexanoate.

d) Wax esters such as beeswax, spermaceti wax and tribehenin wax.

e) Sterols esters, of which cholesterol fatty acid esters are examples thereof.

f) Sugar ester of fatty acids such as sucrose polybehenate and sucrose polycottonseedate.

Of particular use also are the $C_{12-15}$ alkyl benzoate esters sold under the Finsolve brand.

Hydrocarbons which are suitable cosmetically acceptable carriers include petrolatum, mineral oil, $C_{11}$-$C_{13}$ isoparaffins, polyalphaolefins, and especially isohexadecane, available commercially as Permethyl 101A from Presperse Inc.

Humectants of the polyhydric alcohol-type can be employed as cosmetically acceptable carriers. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, glycerol, ethoxylated glycerol, propoxylated glycerol and mixtures thereof. The amount of humectant may range anywhere from 0.5 to 50%, preferably between 1 and 15% by weight of the composition. Most preferred is glycerol (also known as glycerin). Amounts of glycerin may range from about 1% to about 50%, preferably from 10 to 35%, optimally from 15 to 30% by weight of the composition.

Besides cosmetically acceptable carriers, the compositions of this invention may include a variety of other functional ingredients. Sunscreen actives may be included in compositions of the present invention. These will be organic compounds having at least one chromophoric group absorbing within the ultraviolet ranging from 290 to 400 nm. Chromophoric organic sunscreen agents may be divided into the following categories (with specific examples) including, p-Aminobenzoic acid, its salts and its derivatives (ethyl, isobutyl, glyceryl esters; p-dimethylaminobenzoic acid); Anthranilates (o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, alpha-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene), Dibenzalacetone and benzalacetophenone; Naphtholsulfonates (sodium salts of 2-naphthol-3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzone, Sulisobenzone, Dioxybenzone, Benzoresorcinol, 2,2', 4,4'-Tetrahydroxybenzophenone, 2,2'-Dihydroxy-4,4'-dimethoxybenzophenone, Octabenzone; 4-Isopropyidibenzoylmethane; Butylmethoxydibenzoylmethane; Etocrylene; and 4-isopropyl-dibenzoylmethane). Particularly useful are: 2-ethylhexyl p-methoxycinnamate, 4,4'-t-butyl methoxydibenzoylmethane, 2-hydroxy-4-methoxybenzophenone, octyidimethyl p-aminobenzoic acid, digalloyltrioleate, 2,2-dihydroxy-4-methoxybenzophenone, ethyl 4-[bis(hydroxypropyl)]aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid and mixtures thereof.

Particularly preferred are such materials as ethylhexyl p-methoxycinnamate, available as Parsol MCX®, Avobenzene, available as Parsol 1789®, Dermablock OS® (octylsalicylate) and Mexoryl SX® (with INCI name of Terephthalylidene Dicamphor Sulfonic Acid).

Amounts of the organic sunscreen agent may range from about 0.1 to about 15%, preferably from about 0.5% to about 10%, optimally from about 1% to about 8% by weight of the composition.

A variety of thickening agents may be included in the compositions. Illustrative but not limiting are Acrylamide/Sodium Acryloyid imethyltaurate Copolymer, Hydroxyethyl Acrylate/Sodium Acryloyidimethyltaurate Copolymer, Aluminum Starch Octenyl Succinate, Polyacrylates (such as Carbomers including Carbopol® 980, Carbopol® 1342, Pemulen TR-2® and the Ultrez® thickeners), Polysaccharides (including xanthan gum, guar gum, pectin, carageenan and sclerotium gums), celluloses (including carboxymethyl cellulose, ethyl cellulose, hydroxyethyl cellulose and methyl hydroxymethyl cellulose), minerals (including talc, silica, alumina, mica and clays, the latter being represented by bentonites, hectorites and attapulgites), magnesium aluminum silicate and mixtures thereof Amounts of the thickeners may range from about 0.05 to about 10%, preferably from about 0.3 to about 2% by weight of the compositions.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, butyl paraben, isobutyl paraben, imidazolidinyl urea, sodium dehydroacetate and benzyi alcohol, The preservatives should be selected having regard for the use of the composition and possible incompatibilities between the preservatives and other ingredients in the emulsion. Preservatives are preferably employed in amounts ranging from 0.01% to 2% by weight of the composition.

Compositions of the present invention may also contain vitamins and flavonoids. Illustrative water-soluble vitamins are Niacinamide, Vitamin $B_2$, Vitamin $B_6$, Vitamin C and Biotin. Among the useful water-insoluble vitamins are Vitamin A (retinol), Vitamin A Palmitate, ascorbyl tetraisopalmitate, Vitamin E (tocopherol), Vitamin E Acetate and DL-panthenol. A particularly suitable Vitamin $B_6$ derivative is Pyridoxine Palmitate. Among the preferred flavonoids are glucosyl hesperidin and rutin. Total amount of vitamins or flavonoids when present in compositions according to the present invention may range from 0.001 to 10%, preferably from 0.01% to 1%, optimally from 0.1 to 0.5% by weight of the composition.

Desquamation agents are further optional components. Illustrative are the alpha-hydroxycarboxylic acids and beta-hydroxycarboxylic acids and salts of these acids. Among the former are salts of glycolic acid, lactic acid and malic acid. Salicylic acid is representative of the beta-hydroxycarboxylic acids. Amounts of these materials when present may range from about 0.1 to about 15% by weight of the composition.

A variety of herbal extracts may optionally be included in compositions of this invention. Illustrative are pomegranate, white birch (*Betula Alba*), green tea, chamomile, licorice, boswellia serrata, olive (*Olea Europaea*) leaf, arnica montana flower, lavandula angustifolia, and extract combinations thereof. The extracts may either be water soluble or water-insoluble carried in a solvent which respectively is hydrophilic or hydrophobic. Water and ethanol are the preferred extract solvents.

Miscellaneous other adjunct cosmetic ingredients that may be suitable for the present compositions include ceramides (e.g. Ceramide 3 and Ceramide 6), conjugated linoleic acids, colorants (e.g. iron oxides), metal (manganese, copper and/or zinc) gluconates, allantoin, palmitoyl pentapeptide-3, amino acids (e.g. alanine, arginine, glycine, lysine, proline, serine, threonine, glumatic acid and mixtures thereof), trimethylglycine, sodium PCA, magnesium aspartate, and combinations thereof. Amounts may vary from 0.000001 to 2% by weight of the composition.

A small amount of emulsifying surfactant may be present. Surfactants may be anionic, nonionic, cationic, amphoteric and mixtures thereof. Levels may range from 0.1 to 5%, preferably from 0.1 to 2%, optimally from 0.1 to 1% by weight. Advantageously the amount of surfactant present should not be sufficient for lather formation. In these instances, less than 2% by weight, preferably less than 1%, and optimally less than 0.5% by weight surfactant is present.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

It should be noted that in specifying any range of concentration or amount, any particular upper concentration can be associated with any particular lower concentration or amount.

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

Examples 1-6

A series of formulas to be used as anti-aging creams based on the present invention is provided in Table I.

TABLE I

| INGREDIENTS | EXAMPLE (Weight %) | | | | | |
|---|---|---|---|---|---|---|
| | 1 | 2 | 3 | 4 | 5 | 6 |
| Abil EM-90 (Cetyl Dimethicone Copolyol) | 2.0 | 2.0 | 1.0 | 1.0 | 1.0 | 1.0 |
| PEG-10 Dimethicone | 1.5 | 0 | 1.0 | 0 | 0 | 1.0 |
| Polyglyceryl Ricinoleate | 2.0 | 1.0 | 0 | 0 | 0 | 0.5 |
| Magnesium Sulfate | 0.5 | 0 | 0 | 0.5 | 0.5 | 0.5 |
| Sucrose Distearate | 0.5 | 0.5 | 0 | 0 | 0 | 0 |
| Glycerin | 8.0 | 0 | 8 | 10 | 10 | 15 |
| Niacinamide | 3.0 | 0 | 0 | 2.0 | 2.0 | 0.5 |
| Parsol ® MCX | 7.5 | 4.0 | 3.5 | 0 | 0 | 3.5 |
| Z-Cote HP-1 (Zinc Oxide) | 3.0 | 1.0 | 0 | 0 | 0 | 0 |
| DC 246 (Cyclohexasiloxane, Cyclopentasiloxane) | 0 | 20 | 20 | 0 | 0 | 0 |
| DC 245 (Cyclopentasiloxane, Cyclotrisiloxane, Cyclohexasiloxane, Cyclotetrasiloxane) | 40 | 0 | 0 | 10 | 30 | 15 |
| DC 9045 Silicone Elastomer Blend (Dimethicone Crosspolymer and Cyclopentasiloxane) | 15 | 40 | 30 | 30 | 20 | 15 |
| Dry Flo Pure 28-1850 (Aluminum Starch Octenylsuccinate, Water) | 5.0 | 0 | 0 | 5.0 | 2.0 | 2.0 |

TABLE I-continued

| INGREDIENTS | EXAMPLE (Weight %) | | | | | |
|---|---|---|---|---|---|---|
| | 1 | 2 | 3 | 4 | 5 | 6 |
| Ganzpearl GMP-0820 ® | 0.8 | 5.0 | 1.0 | 0.3 | 1.0 | 0.5 |
| Timiron ® MP-111 (Titanium Dioxide Coated Mica) | 1.0 | 0.8 | 0.6 | 0.6 | 0.6 | 0.5 |
| Barium Sulfate (Single-Crystal Flat Platy) | 0.2 | 0.2 | 0.4 | 0.4 | 0.8 | 0.8 |
| Pomegranate Extract | 0.1 | 0.1 | 0.3 | 0.3 | 0.1 | 0 |
| Conjugated Linoleic Acid | 0.1 | 0.1 | 0.5 | 1.0 | 2.0 | 0.3 |
| Fragrance | 0.5 | 0.5 | 0.5 | 0.8 | 0.8 | 0.8 |
| Methylparaben | 0 | 0.2 | 0.2 | 0 | 0.2 | 0 |
| Propylparaben | 0 | 0.1 | 0.1 | 0 | 0.1 | 0 |
| Phenoxyethanol | 0.4 | 0 | 0 | 0 | 0 | 0.2 |
| Glydant Plus Liquid ® (DMDM Hydantoin, Iodopropynyl Butylcarbamate) | 0.2 | 0.2 | 0.2 | 0.4 | 0.4 | 0.4 |
| Water | Balance | Balance | Balance | Balance | Balance | Balance |

Examples 7-11

In this Example a series of moisturizing skin cream/lotion is reported under Table II which are useful in the present invention.

In a suitable vessel, the Phase A components are blended together with a suitable mixer (e.g., Tekmar model RW20DZM) and mixing is continued until all of the components are dissolved. Then, the Phase B components are blended together in a suitable vessel and are milled using a

TABLE II

| INGREDIENTS | EXAMPLE (Weight %) | | | | |
|---|---|---|---|---|---|
| | 7 | 8 | 9 | 10 | 11 |
| PHASE A | | | | | |
| Allantoin | 0.1 | 0.1 | 0.1 | 0.1 | 0.1 |
| Disodium EDTA | 0.1 | 0.1 | 0.1 | 0.1 | 0.1 |
| Ethyl Paraben | 0.2 | 0.2 | 0.2 | 0.2 | 0.2 |
| Propyl Paraben | 0.1 | 0.1 | 0.1 | 0.1 | 0.1 |
| Butylated Hydroxy Toluene | 0.015 | 0.15 | 0.01 | 0.015 | 0.015 |
| Dexpanthenol | 1.0 | 0.5 | 1.0 | 1.0 | 1.0 |
| Glycerin | 7.5 | 10.0 | 15.0 | 7.5 | 5.0 |
| N-undecylenoyl-L-phenylalanine | 2.0 | 0.5 | 1.0 | 4.0 | 1.0 |
| Hexamidine Isethionate | 0.0 | 0.1 | 0.1 | 0.0 | 1.0 |
| Niacinamide | 0 | 3.5 | 5.0 | 2.0 | 2.0 |
| Palmitoyl-pentapeptide (1) | 0 | 0 | 0 | 0.0004 | 0.0003 |
| Phenylbenzimadazole Sulfonic Acid | 0 | 0 | 0 | 0 | 1.0 |
| Benzyl Alcohol | 0.25 | 0.25 | 0.25 | 0.25 | 0.25 |
| Triethanolamine | 0.8 | 0.2 | 0.40 | 1.60 | 1.0 |
| Green Tea Extract | 1.0 | 1.0 | 1.0 | 1.0 | 1.0 |
| N-Acetyl Glucosamine | 0.0 | 5.0 | 2.0 | 0.0 | 5.0 |
| Sodium Metabisulfite | 0.1 | 0.1 | 0.1 | 0.1 | 0.1 |
| Water | Balance | Balance | Balance | Balance | Balance |
| PHASE B | | | | | |
| Cyclopentasiloxane | 15.0 | 15.0 | 18.0 | 15.0 | 15.0 |
| Barium Sulfate (Single-Crystal Flat Platy) | 0.5 | 0.5 | 0.75 | 0.5 | 0.5 |
| Ganzpearl GMP-0820 ® | 0.5 | 0.5 | 0.75 | 0.3 | 0.8 |
| PHASE C | | | | | |
| C12–C15 Alkyl Benzoate | 1.5 | 0 | 0 | 1.5 | 1.5 |
| Dipalmitoyl Hydroxyproline | 0 | 1.0 | 0 | 0 | 1.0 |
| Salicylic Acid | 1.5 | 0 | 0 | 0 | 0 |
| PPG-15 Stearyl Ether | 4 | 0 | 0 | 0 | 0 |
| Vitamin E Acetate | 0.5 | 0 | 1.0 | 0.5 | 0.5 |
| Retinyl Propionate | 0.0 | 0 | 0 | 0.2 | 0.2 |
| Phytosterol | 0.0 | 0.0 | 1.0 | 5.0 | 3.0 |
| PHASE D | | | | | |
| KSG-21 Silicone Elastomer (2) | 4.0 | 4.0 | 5.0 | 4.0 | 4.0 |
| Dow Corning 9040 Silicone Elastomer | 15.0 | 15.0 | 12.0 | 15.0 | 15.0 |
| Dimethicone Copolyol (3) | 0.5 | 0 | 0 | 0.5 | 0.5 |
| Polymethylsilsesquioxane | 2.5 | 2.5 | 2.0 | 2.5 | 2.5 |
| Fragrance | 0.2 | 0.2 | 0.2 | 0.2 | 0.2000 |

(1) palmitoyl-pentapeptide = palmitoyl-lysine-threonine-threonine-lysine-serine available from Sederma.
(2) KSG-21, an emulsifying silicone elastomer available from Shin Etsu
(3) Abil EM-97 available from Goldschmidt Chemical Corporation suitable mill (e.g., Tekmar RW-20) for about 5 minutes. The Phase C components are then added to the Phase B mixture with mixing. Then, the Phase D components are added to the mixture of Phases B and C and the resulting combination of Phase B, C, and D components is then mixed using a suitable mixer (e.g., Tekmar RW-20) for about 1 hour. Then, Phase A is slowly added to the mixture of Phases B, C, and D with mixing. The resulting mixture is then continually mixed until the product is uniform. The resulting product is then milled for about 5 minutes using an appropriate mill (e.g., Tekmar T-25).

Examples 12-18

A series of formulas were investigated for their optical properties. These are recorded in Table III below.

TABLE III

| | Sample No. (Weight %) | | | | | | |
|---|---|---|---|---|---|---|---|
| Component | 12 | 13 | 14 | 15 | 16 | 17 | 18 |
| Phase A | | | | | | | |
| DC 246* | 9.625 | 9.625 | 9.625 | 9.625 | 9.625 | 9.625 | 9.625 |
| DC 245** | 8.105 | 8.105 | 8.105 | 10.605 | 8.105 | 10.105 | 8.105 |
| Z-Cote HP-1 (Zinc Oxide) | 2.000 | 2.000 | 2.000 | 2.000 | 2.000 | 2.000 | 2.000 |
| Phase B | | | | | | | |
| DC 9045 Silicone Elastomer Blend | 45.570 | 45.570 | 45.570 | 45.570 | 45.570 | 45.570 | 45.570 |
| Phase C | | | | | | | |
| Cetyl Dimethicone Copolyol | 1.000 | 1.000 | 1.000 | 1.000 | 1.000 | 1.000 | 1.000 |
| Phase D | | | | | | | |
| Ganzpearl GMP-0820 (Acrylates Crosspolymer) | 2.000 | 2.000 | 2.000 | 0.000 | 2.000 | 0.000 | 2.000 |
| Timiron MP-111*** | 1.000 | 1.000 | 1.000 | 1.000 | 1.000 | 1.000 | 1.000 |
| Barium Sulfate HL (Single Crystal Platy) | 0.500 | 0.000 | 0.000 | 0.000 | 0.000 | 0.500 | 0.000 |
| Barium Sulfate LLD-5 (Spherical) | 0.000 | 0.500 | 0.000 | 0.000 | 0.000 | 0.000 | 0.000 |
| Barium Sulfate (KOBO) | 0.000 | 0.000 | 0.500 | 0.000 | 0.000 | 0.000 | 0.000 |
| Barium Sulfate HG | 0.000 | 0.000 | 0.000 | 0.000 | 0.000 | 0.000 | 0.500 |
| Phase E | | | | | | | |
| Deionized Water | 10.000 | 10.000 | 10.000 | 10.000 | 10.000 | 10.000 | 10.000 |
| Glycerin | 15.000 | 15.000 | 15.000 | 15.000 | 15.000 | 15.000 | 15.000 |
| Glydant Plus Liquid**** | 0.200 | 0.200 | 0.200 | 0.200 | 0.200 | 0.200 | 0.200 |
| Phase F | | | | | | | |
| Aluminum Starch Octenylsuccinate | 5.000 | 5.000 | 5.000 | 5.000 | 5.000 | 5.000 | 5.000 |

*Cyclohexasiloxane and cyclopentasiloxane.
**Cyclopentasiloxane, cyclotriloxane, cyclohexasiloxane and cyclotetrasiloxane
***Titanium dioxide coated mica.
****DMDM Hydantoin, Iodopropynyl Butyl Carbonate, Butylene Glycol and Water The formulas in Table III were blended in the following manner. Phase A was prepared by adding zinc oxide into DC 245 and DC 246 until dispersed, Phase A was then added to Phase B in a main reactor under propeller mixing. Phase C was then added to Phase A/B while maintaining mixing for a 10 minute period until uniform. Phase D powders were then added to Phase A/B/C individually, using slow addition to avoid clumping. Premixed Phase E was added and mixed until uniform. Phase F was then added to the other phases under slow addition to avoid clumping. The batch was then homogenized for 10 minutes.

Optical Measurements

Opacity is the measure of intensity attenuation of a transmitted light beam shone perpendicular to a medium or film. The higher the direct beam attenuation, the greater will be the opacity. The source of the light beam attenuation is two fold: A) Some of the original light is reflected back from the film/medium. This gives the film/medium a true white/opaque appearance with great hiding power. Using pigment-grade $TiO_2$ in a formulation will give the effect. B) Some of the light is deflected from the straight beam path but still transmitted through the film/medium. In effect, the film/medium goes from being transparent to translucent, creating a "blurred" image. Another term for this is soft focus.

Procedure: Apply (or draw down) a 3 mil (76.2 μm) film of a formulation using a draw down bar on to a plastic overhead transparency sheet. Let the film dry for 2 hours at room temperature. Take the coated overhead transparency and place it in an Instrument Systems goniospectrophotometer.

Set the light source and detector arrayed in a straight line perpendicular to the coated transparency. The light source (set at 209 million Watt-nm/cm$^2$, which serves as a reference for all Transmission Intensity values reported herein) is turned on and the measurement of the transmitted light intensity is made. Further measurements are made by moving the detector 10, 30, 40 and 50 degrees away from the direct transmission normal. These values indicate the extent of soft focus light scattering. The Reflectance or "radiance" of a product is determined in the same way as opacity/soft focus light scattering, except for the positions of the light source and detector. The detector is 20 or 30 degrees on one side of the normal/perpendicular, while the light source is 20 degrees on the other side. To determine the extent of the intensity attenuation, compare the intensity value to that of an uncoated overhead transparency. The difference between these two values is the extent of the attenuation or opacity.

Results: The effect of certain components on the optical properties of the compositions was evaluated by testing formulations with those components removed. Results are reported in Table IV. The Acceptability range values are for facial color management which provides soft focus but minimizes shininess and regulates opacification. Numbers in bold are values found outside the Acceptability ranges.

experiments where either the single crystal platy barium sulfate or the Ganzpearl or both components were absent from the base formula. In all these experiments, there was a significant deviation from Acceptability range.

What is claimed is:

1. A cosmetic composition comprising:
    (i) from about 0.01 to about 10% of single-crystal platy barium sulfate by weight of the composition;
    (ii) from about 0.1 to about 10% of a water-insoluble powdered acrylic polymer in porous particle form; and
    (iii) a cosmetically acceptable carrier;
    wherein the composition is a water-in-oil emulsion being emulsified by a dimethicone copolyol surfactant and the single-crystal platy barium sulfate has a number average particle size ranging from 11 to 12 micron and is not coated with any organic coating.

2. The composition according to claim 1 wherein the acrylic polymer is a methyl methacrylate crosspolymer.

3. The composition according to claim 1 wherein the barium sulfate is present in an amount from about 0.1 to about 1% by weight of the composition.

TABLE IV

| | Sample No. (W-nm/cm$^2$) | | | | | | | Acceptability Transmission Intensity (Watt-nm/cm$^2$) |
|---|---|---|---|---|---|---|---|---|
| | 12 | 13 | 14 | 15 | 16 | 17 | 18 | |
| Transmission Angle in degrees | | | | | | | | |
| 0 | 6.11 M | 3.36 M | 5.16 M | 8.45 M | 3.82 M | 5.52 M | 6.52 M | 4 to 7 million |
| 10 | 1.02 M | 835.2 K | 987.5 K | 967.8 K | 1.12 M | 1.15 M | 1.00 M | 1 to 2 million |
| 30 | 129.72 M | 139.91 K | 135.9 K | 124.9 K | 132.9 K | 124.72 K | 123.52 K | 120 to 140 thousand |
| 40 | 80.51 K | 95.86 K | 85.91 K | 78.04 K | 80.50 K | 75.25 K | 74.15 K | 60 to 85 thousand |
| 50 | 55.75 K | 64.75 K | 58.91 K | 54.12 K | 56.40 K | 52.55 K | 51.65 K | 40 to 60 thousand |
| Reflection Angle in degrees | | | | | | | | |
| 20 | 147.66 K | 92.44 K | 128 K | 140.51 K | 111.26 K | 161.2 K | 167.2 K | 140 to 160 thousand |
| 30 | 109.40 K | 84.68 K | 102.0 K | 107.39 K | 93.03 K | 115.2 K | 116.2 K | 90 to 110 thousand |

Samples 12, 13, 14 and 18 represent a base formula with a combination of different barium sulfates each with a powdered acrylic polymer (Ganzpearl GMP-0820). The respective barium sulfates are HL (single crystal platy) with average particle size 11-12 micron (Sample 12), LLD-5 (spherical) with average particle size 1 micron or less (Sample 13), Kobo (single crystal platy) with average particle size 5 micron (Sample 14), and HG (single crystal platy) with average particle size 20 micron (Sample 18). In almost all Transmission Angle and Reflection Angle measurements the value result for Sample 13 was outside Acceptability parameters. It is evident that a spherical barium sulfate is significantly inferior to the single crystal platy variety represented by the inventive Sample 12. Although useful for the present invention, platy barium sulfate of 5 micron and of 20 micron (Samples 14 and 18) performed slightly less well than the 11-12 micron size barium sulfate. Samples 15, 16 and 17 represent control 4. The composition according to claim 1 wherein the powdered acrylic polymer has a porosity as measured by Oil Absorbance (Castor Oil) ranging from about 90 to about 500 ml/100 grams.

5. The composition according to claim 4 wherein the powdered acrylic polymer in porous particle form has particle density ranging from about 0.08 to 0.55 g/cm$^3$.

6. The composition according to claim 1 wherein the cosmetically acceptable carrier comprises from about 30 to about 80% water by weight of the composition.

7. The composition according to claim 1 wherein the cosmetically acceptable carrier comprises from about 50 to about 70% water by weight of the composition.

\* \* \* \* \*